(12) United States Patent
Filipov

(10) Patent No.: US 11,382,675 B2
(45) Date of Patent: Jul. 12, 2022

(54) SURGICAL METHOD FOR BIPLANE SCREW FIXATION OF FEMORAL NECK FRACTURES (CALCAR BUTTRESSED SCREW FIXATION)

(71) Applicant: EKTA-Sofia Ltd., Sofia (BG)

(72) Inventor: Orlin Filipov, Sofia (BG)

(*) Notice: Subject to any disclaimer, the term of this patent is extended or adjusted under 35 U.S.C. 154(b) by 109 days.

(21) Appl. No.: 16/837,735

(22) Filed: Apr. 1, 2020

(65) Prior Publication Data

US 2021/0307795 A1    Oct. 7, 2021

(51) Int. Cl.
  *A61B 17/74* (2006.01)
  *A61B 17/86* (2006.01)
  *A61B 17/56* (2006.01)

(52) U.S. Cl.
  CPC ............ *A61B 17/74* (2013.01); *A61B 17/864* (2013.01); *A61B 17/8625* (2013.01); *A61B 2017/564* (2013.01)

(58) Field of Classification Search
  CPC ............ A61B 17/74–748; A61B 17/17; A61B 17/1721
  See application file for complete search history.

(56) References Cited

U.S. PATENT DOCUMENTS

| | | | |
|---|---|---|---|
| 2,243,717 A | | 5/1941 | Moreira |
| 2,531,734 A | * | 11/1950 | Hopkins ............ A61B 17/1721 606/97 |
| 4,383,527 A | * | 5/1983 | Asnis ................ A61B 17/1721 606/96 |
| 4,488,543 A | * | 12/1984 | Tornier ............. A61B 17/746 606/65 |

(Continued)

FOREIGN PATENT DOCUMENTS

| | | |
|---|---|---|
| EP | 004739241-001 | 3/2018 |
| EP | 004739241-0002 | 3/2018 |

OTHER PUBLICATIONS

Filipov,O.,Stoffel,K.,Gueorguiev,B.,Sommer,C.(2017). Femoral neck fracture osteosynthesis by the biplane double supported screw fixation method (BDSF) reduces the risk of fixation failure. Clinical outcomes in 207 patients. JArchOrthopTraumaSurg,137(6):779-788. (Year: 2017).*

(Continued)

*Primary Examiner* — Eduardo C Robert
*Assistant Examiner* — Michelle C Eckman
(74) *Attorney, Agent, or Firm* — Miller Law Group, PLLC

(57) ABSTRACT

The modified method of Biplane Double-supported Screw Fixation (Modified BDSF) (Calcar buttressed screw fixation) of femoral neck fractures is disclosed. BDSF is applied using three standard bone screws laid in two vertical oblique planes in the femoral neck: the inferior (distal) screw is placed at an obtuse angle in the posterior oblique plane, and touched on the inferior (distal) and on the posterior cortices of the femoral neck; the middle screw and the proximal screw are laid in the anterior oblique plane and in parallel to each-other, with the middle screw touched on the distal femoral neck cortex. With BDSF of the three screws, two are weight-bearing and act as console beams: the distal screw and the middle screw, each of them having two supporting points in the distal fragment: medial (on the distal femoral neck cortex), and lateral (in the place of screw entry into the lateral femoral cortex).

15 Claims, 2 Drawing Sheets

(56) References Cited

U.S. PATENT DOCUMENTS

| | | |
|---|---|---|
| 4,858,601 A | 8/1989 | Glisson |
| 4,950,270 A | 8/1990 | Bowman et al. |
| 5,169,400 A | 12/1992 | Muhling et al. |
| 5,217,462 A | 6/1993 | Asnis et al. |
| 5,423,819 A | 6/1995 | Small et al. |
| 5,431,651 A | 7/1995 | Goble |
| 5,443,509 A | 8/1995 | Boucher et al. |
| 5,498,265 A | 3/1996 | Asnis et al. |
| 5,549,677 A | 8/1996 | Durr et al. |
| 5,584,836 A | 12/1996 | Ballintyn et al. |
| 5,743,914 A | 4/1998 | Skiba |
| 5,891,146 A | 4/1999 | Simon et al. |
| 6,592,587 B1 | 7/2003 | Roger |
| 6,635,059 B2 | 10/2003 | Randall et al. |
| 6,981,974 B2 | 1/2006 | Berger |
| 7,207,994 B2 | 4/2007 | Mahos et al. |
| 7,731,738 B2 | 6/2010 | Jackson et al. |
| 8,267,975 B2 | 9/2012 | McCombs et al. |
| 8,623,060 B2 | 1/2014 | Mahos et al. |
| 9,301,790 B2 | 4/2016 | Dorawa et al. |
| 9,681,904 B2 * | 6/2017 | Wolf .................. A61B 17/808 |
| 2003/0236527 A1 * | 12/2003 | Kawakami ......... A61B 17/1721 606/96 |
| 2011/0257657 A1 * | 10/2011 | Turner ................ A61B 17/175 606/103 |
| 2015/0066041 A1 * | 3/2015 | Kim ................... A61B 17/1721 606/96 |
| 2018/0296244 A1 * | 10/2018 | Kim ................... A61B 17/1721 |
| 2019/0029743 A1 * | 1/2019 | Rocci ................. A61B 17/842 |

OTHER PUBLICATIONS

1. Filipov, O. (2011) Biplane double-supported screw fixation (F-technique): a method of screw fixation at osteoporotic fractures of the femoral neck. Eur J Orthop Surg Traumatol, 21(7): 539-543.
2. Filipov, O., Stoffel, K., Gueorguiev, B., Sommer, C. (2017). Femoral neck fracture osteosynthesis by the Biplane Double-supported Screw Fixation method (BDSF) reduces the risk of fixation failure. Clinical outcomes in 207 patients. J Arch Orthop Trauma Surg, 137(6): 779-788.
1. Filipov, O. (Jun. 1, 2019) Biplane Double-supported Screw Fixation of Femoral Neck Fractures: Surgical Technique and Surgical Notes. J Am Acad Orthop Surg; 27(11):e507-515. doi: 10.5435/JAAOS-D-17-00117. PMID: 30399029.
1. Stryker, Mahwah, NJ, USA. (2013). Stryker surgical techniques, https://www.strykermeded.com/media/1533/asnisiii-cannulated-screw_982187_rev5.pdf. Last accessed: Apr. 30, 2018.
3. U.S. Copyright Office Receipt, Case #1-6339893831, case date: Mar. 2, 2018, title: Scientific project concerning device for biplane fixation of femoral neck fractures Applicant's Internal Tracking: A7411104520a.
Ahmed El Soudy Hawam et al.: "Role of Biplane Double Support Screw Fixation for Fracture Neck of Femur in Elderly Population", in AL-Azhar International Medical Journal, Jun. 2020, pp. 81-84.
Dr. Gaurav Menwal et al.: Appraisal of Clinical Outcome of Biplane Double Supported Screw Fixations (BDSF) for Femoral Neck Fractures, Indian Journal of Applied Research, vol. 11, Issue 7, Jul. 2021, p. 1, ISSN No. 2249-555X.
Anoop Kalla et al.: "Role of Biplane Double Supported Screw Fixation for Fracture Neck Femur in Elderly Population: A Prospective Study", The Open Orthopaedics Journal, vol. 12, Jul. 5, 2018, p. 514.
Lin Tianye et al.: "Finite Element Analysis of Different Internal Fixation Methods for the Treatment of Pauwels Type III Femoral Neck Fracture", Biomedicine & Pharmacotherapy, Nov. 16, 2018, pp. 1-8.
K.K. Arvind Manoj et al.: "Calcar Buttressed Screw Fixation for Femoral Neck Fracture", International Journal of Research in Orthopaedics, Jan.-Feb. 2019, vol. 5, Issue 1, p. 145.
Siddharth Gupta et al.: "Biplanar Double-Supported Screw Fixation Method in Osteoporotic Neck of Femur Fractures", J. Evolution Med. Dent. Sci., vol. 8, Issue 15, Apr. 15, 2019, p. 1251.
Shiyuan Lin et al.: "Modified F Configuration in the Treatment of Pauwels Type III Femoral Neck Fracture: a Finite Element Analysis", Research Square, p. 1.
Dr. R. Karthik: "Functional and Radiological Outcome of Neck of Femur Fracture Treated by Biplane Double Supported Screw Fixation Method", Dissertation submitted to the Tamilnadu Dr. M.G.R. Medical University Chennai 600032, p. 1
Dr. M. Kabilan: "Comparison of Radiological and Functional Outcome of Internal Fixation of Fracture Neck of Femur with Cancellous Screw Using Conventional Method (FQPP) and Biplanar Double Supporting Screw Fixation (BDSF)", Dissertation submitted to the Tamilnadu Dr. M.G.R. Medical University Apr. 2020, Registration No. 221712253, p. 1.

* cited by examiner

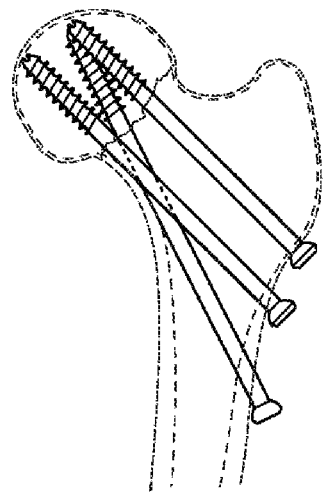
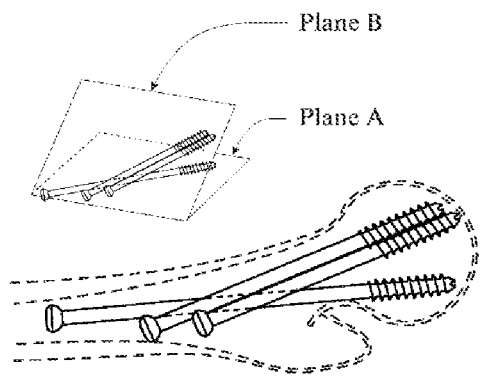
Fig. 1A Fig. 1B
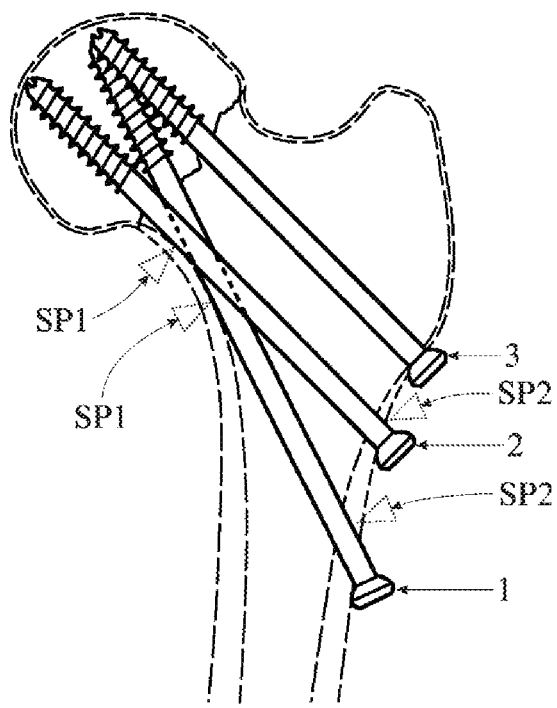
Fig. 2

SURGICAL METHOD FOR BIPLANE SCREW FIXATION OF FEMORAL NECK FRACTURES (CALCAR BUTTRESSED SCREW FIXATION)

FIELD

The present document generally relates to a method for the fixation of fractures along the femoral neck that enables the implant to be used for the fixation of bone fractures.

BACKGROUND

Orthopedic bone screws, either cannulated screws or non-cannulated screws, or rarely other types of implants (like spring-nails, etc.) have been used for the internal fixation of femoral neck fractures, and a placement of three cannulated screws in-parallel to each-other through the femoral neck has become the preferred treatment for such fractures.

Femoral neck is exposed to compressive forces of about 2.4 times body weight (BW) and anteroposterior bending of about 2.6 times BW. For the operative fixation of femoral neck fractures, cannulated screws are usually preferred. However, the poor outcomes following conventional fixation with three parallel cannulated screws are still unacceptably high and reaching up to 46% (Rogmark and Johnell 2006, Gjertsen et al. 2010).

With the conventional fixation, three cannulated screws are placed in parallel to each other and parallel to the femoral neck axis, fixing the fracture of the femoral neck. Usually inverted triangle configuration is used (one screw placed inferior in the femoral neck and two screws superior). The inferior screw is supported (touched) on the inferior neck cortex and the supero-posterior screw is supported on the posterior neck cortex (Asnis 1985, Swiontkowski 1994; Lindequist et al., 1993; Thiele et al., 2007, etc.).

However, due to the femoral anatomy, when the screws are placed in parallel, they are inclined at an angle of 120-125° to the diaphyseal axis, following the inclination of the femoral neck, and also their entry holes in the bone are located within the thin and fragile cortex near the Greater trochanter. Moreover, the three screw entry-holes are located pretty close to each other—at a distance of about 7 mm apart of each-other, thus the screws are deprieved of a solid lateral supporting point. Consequently, these implants act as a lever of first class (with a medial support only) and hardly as a console beam, therefore, this type of fixation is associated with up to a 46% rate of complications (Rogmark and Johnell, 2006; Gjertsen et al., 2010), and patients are usually not allowed to full weight bear immediately. Furthermore, the small distances of less than 7 mm between the screw holes on the lateral cortex represent a major stress-riser and allows also for rotation instability when parallel screw fixation is used.

Femoral neck fractures can be fixed more effectively by the novel BDSF method, described here below (FIGS. 1A & 1B, 2 and 3), compared to conventional fixation with parallel screws. Based on clinical evidence and laboratory testing, the method of Biplane double—supported screw fixation (BDSF), (Calcar buttressed screw fixation) is deemed to provide much better osteosynthesis stability and clinical outcomes than conventional fixation (Filipov, 2011; Filipov et al., 2017; Galal and Nagy, 2017; Kalia et al., 2018; Gupta et al., 2019), confirmed in two biomechanical experiments (Filipov and Gueorguiev, 2015; Kean Fa-Chuan et al., 2019) and confirmed also in a finite element model analysis (Tianye et al., 2019).

SUMMARY OF THE INVENTION

According to one aspect of the invention, there is provided a method of fixating a neck fracture of a femur using a modified Biplane Double-Supported Screw Fixation technique (Calcar buttressed screw fixation), said method comprising implanting three fixing screws in positions that, from a lateral view, occupy a neck of said femur in two vertical oblique planes which diverge medially towards a head of said femur at an angle of 15-40° to each-other, and, from among said three fixing screws, implanting an inferior first screw (1) in a posterior one of said oblique planes, and implanting a middle second screw (2) and a superior third screw (3) in an anterior one of said oblique planes.

BRIEF DESCRIPTION OF THE DRAWINGS

FIG. 1A illustrates a femoral neck fracture fixed using a modified method of Biplane Double-supported Screw Fixation (Modified BDSF method), (Calcar buttressed screw fixation) of the present invention, as viewed in an anterior to posterior direction (antero-posterior view), with the femoral bone depicted with large dashed lines.

FIG. 1B illustrates the fixated femoral neck fracture of FIG. 1A as viewed in a lateral to medial direction (lateral view), with the femoral bone depicted with large dashed lines, and with an inset view illustrating reference planes each occupied by different subset of three fixing screws used in said fixation.

FIG. 2 illustrates the same femoral neck fracture fixation of FIG. 1A, as viewed in an anterior to posterior direction, with the femoral bone is depicted with large dashed lines, and screw supporting points on the femoral cortical wall denoted by triangles shown in fine dashed lines.

DETAILED DESCRIPTION

Figure 3:
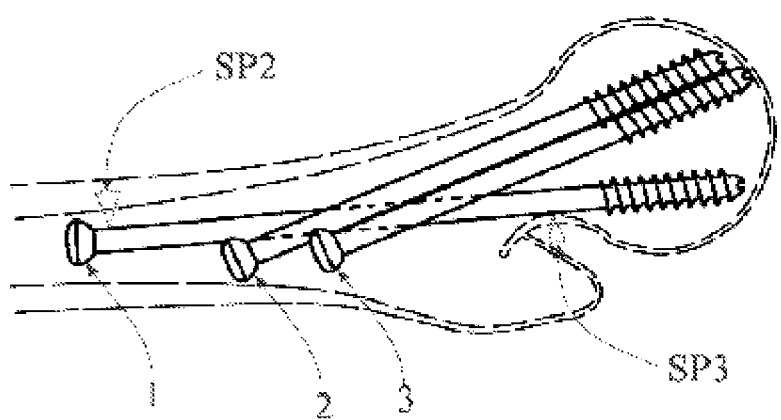
FIG. 3 illustrates the same femoral neck fracture fixation of FIG. 1B, as viewed in a lateral to medial direction, with the femoral bone again depicted with large dashed lines, and screw supporting points again denoted by triangles shown in fine dashed lines.

A method developed for the fixation of femoral neck fractures aiming to achieve improved fixation stability and high bone union rate is disclosed. Three standard bone screws are used for surgical fixation of femoral neck fractures applying the modified method of Biplane Double-supported Screw Fixation (Modified BDSF method), (Calcar buttressed screw fixation).

The BDSF method can be applied using any kind of orthopedic screws or similar implants, having a thread diameter ranging from 5.0 to 8.0 mm or other diameters; thread lengths of 15-32 mm or other thread lengths or no thread (e.g., implants with expandable spikes on the tip), and a shaft diameter of 4.5-5.5 mm or other diameters, with the screw lengths ranging from 75 mm to 140 mm. However, it is preferable the screws (implants) to be cannulated to allow for their easier orientation in the bone during insertion, because the proper orientation of the screws and their proper support on the cortex is very important for the BDSF biomechanics, providing the strongest possible fixation strength achieved with bone screws.

A number of three such screws (implants) are used to fix a femoral neck fracture applying the modified BDSF method.

The Novel Method—the Modified Method of Biplane Double-Supported Screw Fixation (Modified BDSF), (Calcar Buttressed Screw Fixation)

After the initial, original description of the method of Biplane Double-supported Screw Fixation (BDSF) in 2011 by Orlin Filipov, several novel and important details have been developed by its author in terms of the screw positioning and also in the operative technique, thus further improving the fixation stability and making the practical performance of this highly effective method much easier in the clinical practice, and described here as the Modified BDSF method (modified BDSF), (Calcar buttressed screw fixation)

The Modified BDSF method. With the Modified BDSF method, the novel concept of biplane positioning makes it feasible to place three cannulated screws at steeper angles to the diaphyseal axis improving their beam function; and also with this steeper position the screw entry points are located much more distally and within the thicker cortical wall of the proximal diaphysis, which improves the lateral support for the screws in the place of their entry holes, turning these screws to act as console beams (FIGS. 1A & 1B, FIG. 2, FIG. 3). With this innovative position the screws are supported on several solid supporting points in the distal (caudal) fragment, providing improved beam function for the fixation construct.

By the principle of biplane positioning, the three screws are laid in two vertical oblique planes that medially diverge towards the femoral head: anterior oblique plane and posterior oblique plane, which can be viewed from the side (on lateral view, FIG. 1B and FIG. 3). As used herein, "Vertical" means the anatomical term 'vertical' (with the human body in upright position, with arms and legs upright). The inferior (distal) screw (1) is placed in the posterior oblique plane (plane A). This screw is inserted at an obtuse angle of 140-165° (usually 150-165°) towards the axis of the femoral diaphysis and touched on the inferior femoral neck cortex (FIG. 1A, FIG. 2) and, touched also on the posterior femoral neck cortex (FIG. 1B, FIG. 3). The other two screws: the middle screw (2) and the superior (proximal, cranial) screw (3) are laid in the anterior oblique plane (plane B) and are placed in parallel to each-other (FIGS. 1A & 1B, FIG. 2). The middle screw (2) is placed in the lower (distal) part of the femoral neck at an angle of about 130° (120-140° towards the diaphyseal axis and touched on the inferior femoral neck cortex (FIG. 1A and FIG. 2). The superior (proximal) screw (3) is placed at about 15 mm (10-30 mm) cranially (proximal) to the middle screw (2) and parallel to it.

In contrast to conventional parallel screw fixation, the method of BDSF has two weight-bearing screws acting as console beams: the inferior (distal) screw (1) and the middle screw (2). Each one of these two screws has two supporting points in the distal (caudal) fragment: medial supporting point (SP1) on the inferior (distal) femoral neck cortex (known as calcar supporting point), and lateral supporting point (SP2) in the place of screw entry into the lateral cortex of the femoral diaphysis. The inferior (distal) screw (1) has also a third supporting point on the posterior cortex of the femoral neck—posterior supporting point (SP3). The most effective component of this fixation is the inferior BDSF-screw (1) placed at an obtuse angle and supported on a large area along the inferior and posterior cortices of the femoral neck following its spiral anterior curve.

Namely, the inferior (distal) screw (1) has 3 supporting points in the inferior (distal) fragment:
1) Supporting point on the inferior (distal) cortical wall of the femoral neck—the medial supporting point for the screw (SP1), or "calcar support";
2) Supporting point on the lateral cortex of the diaphysis in the screw entry point into the bone—the lateral supporting point for the screw (SP2);
3) Supporting point on the posterior cortex of the femoral neck—the posterior supporting point for the screw (SP3). The spiral anterior curve of the femoral neck allows for the distal screw (1) to be touched on the cortical wall simultaneously at two (medial) supporting points: SP1 and SP3.

The middle screw (2) has 2 supporting points in the inferior (distal) fragment:
1) Supporting point on the inferior (distal) cortical wall of the femoral neck—the medial supporting point for the screw (SP1), or "calcar support";
2) supporting point on the lateral cortex of the diaphysis into the screw entry point in the bone—the lateral supporting point for the screw (SP2).

The proximal screw (3) has no cortical supporting points—it has an anti-rotation function and it also resists on tension forces.

The screw positioning in two oblique planes makes it feasible for one of the screws—the distal screw (1) to be placed at an increased angle towards the femoral diaphyseal axis. Thus, the entry point of this screw is placed much more distally in the solid lateral cortex of the femoral diaphysis. The thick cortical wall at the place of the screw entry provides a firm lateral supporting point for this screw (SP2), which is much more stable compared to the lateral supporting point for the conventional parallel screws located in the fragile cortex in the Greater trochanter region.

In the hip joint there are two main load directions: the vertical load (in a standing position) and the antero-posterior bending load (when standing up/sitting down or climbing) which is the more dangerous one for the fixation construct.

Function

Two screws, the inferior (distal) screw (1) and the middle screw (2), each of them supported on two supporting points: medial supporting point (SP1) and lateral supporting point (SP2) act as console beams when carrying the axial load (with the patient in a standing position), while the superior screw (3) resists the tension in the superior (proximal) side of the fixation construct. In the lateral view (viewed from lateral to medial), the inferior (distal) screw (1), supported on both the posterior neck cortex (posterior supporting point, SP3) and its lateral supporting point (SP2), acts as a console beam resisting to the powerful antero-posterior bending load (with the patient standing up/sitting down/climbing), while the two screws in the anterior oblique plane—the middle screw (2) and the superior screw (3) resists the tension on the anterior aspect of the construct. Moreover, achieving posterior cortical support by using an obtusely placed screw [the inclination of the distal BDSF-screw (1) is usually 150-165° ] substantially improves construct resistance to antero-posterior (AP) bending forces and moments, compared to the conventional parallel screw fixation (which inclination is 120-130°), (Walker et al., 2007). As we said, biomechanically the most effective component is the inferior screw (1) placed at an obtuse angle and supported on a large area along the inferior and posterior cortex of the femoral neck following its spiral anterior curve, which provides a very strong calcar support for this screw. Thereby, the modified BDSF (like the BDSF) provides the strongest possible inferior—posterior cortical support for the fixation construct, which allows for immediate full weight bearing post-surgery following this highly effective procedure (Filipov et al., 2017; Galal and Nagy, 2017; Kalia et al., 2018; Gupta et al., 2019). Furthermore, the modified BDSF as well as the BDSF implements two calcar-buttressed screws: the inferior screw (1) and middle screw (2), oriented in different coronal inclinations, which provide constant fixation stability during various weight-bearing activities and load directions. Moreover, their medial supporting points are located 10-20 mm apart, thereby distributing the axial load over a larger area of the inferior cortical wall, in contrast to the conventional parallel screw fixation where the stress is concentrated on a single spot.

The inferior screw (1) is placed at a highly increased angle of 150-165° (from 140 to 165°), thus the screw acts in a direction close to the direction of the loading force in walking, which ensures better results for the screw in its role as a beam, because the influence of its sagging decreases. Moreover, when the screw is placed at a steeper angle, the distance between the two supporting points also increases compared to conventional parallel screw fixation. Due to such increase in the distance between the two supporting points, the weight borne by the supporting points on the femoral cortex is reduced, compared to the conventional parallel screw fixation, calculated applying the widely known equilibrium equations for a beam (Filipov, 2011). Another advantage of the BDSF method is that the entry points of the screws are positioned wide apart from each-other, which ensures the tensile forces to spread over a larger surface of the lateral femoral cortex, thus the risk of its fracturing decreases significantly, compared to the conventional parallel screw fixation. Much stronger antero-posterior, varus, and rotational fixation stability are created at the fracture site with BDSF, compared to conventional parallel screw fixation.

This princilpe of fixation of BDSF and the modified BDSF is intended to be an universal principle of fixation of most kinds of tubular cantilevers with a solid end. Such a tubular cantilever with a solid end is the proximal femur where the head and the neck of the femur overhang away from the diaphysis as a cantilever supporting the body weight. The femoral head is composed of a comparatively dence cancellous bone, and the other elements—the femoral neck and the femoral diaphysis are tubular elements.

The surgical procedure of the Modified BDSF method (Filipov 2019) described below is based on the BDSF method (Filipov, 2011; 2017). After the original description of the method of BDSF in 2011, there are few novel details in terms of the screw positioning and in the operative technique, which have been modified by its author, improving further the fixation stability and making the practical performance of this highly effective method in the clinical practice much easier.

The surgical procedure of the Modified BDSF method (Calcar buttressed screw fixation) is the following (Filipov, 2019, JAAOS). Through appropriate skin incision, a stripping of the periosteum over a distance of 4-7 cm along the lateral diaphysis is performed, however this procedure can also be performed without stripping of the periosteum, but by retraction of the soft tissues with or without the use of protection sleeves or cannulas. The guide wire for the middle screw is inserted in the anterior oblique plane. The entry point of this wire is in the lateral cortex (preferably in the posterior third of the lateral cortex) and 3-4 cm caudally (distally) to the lower border of the Greater trochanter (supporting point SP2) depending on the femoral neck-shaft angle (caput-collum-diaphyseal angle, CCD angle) and the femur size. This wire is inclined in an antero-cranial (antero-proximal) direction, at an angle of 120-140° to the diaphyseal axis (130-135° for a normal femur; 120-130° for a varus femur, and 135-140° for a valgus femur), so that after touching the inferior (caudal) neck cortex tangentially (supporting point SP1), the guide wire enters the infero-anterior aspect of the femoral head. On antero-posterior view (when the bone is viewed from anterior to posterior or from posterior to anterior, using radiographic, x-ray, fluoroscopic or other imaging methods, AP-view), the tip of this guide wire is seen (projects) in the inferior (distal) third part of the femoral head. On lateral view (when the bone is viewed from lateral to medial or from medial to lateral, using radiographic, x-ray, fluoroscopic or other imaging methods), the tip of this guide wire is seen (projects) in the anterior third part of the femoral head and neck (the guide wire is in the anterior oblique plane).

The guide wire for the superior (cranial, proximal) screw is inserted in the anterior oblique plane, with an entry point in the lateral cortex (preferably in the posterior third of the lateral cortex) and at a distance of 1-3 cm superior (cranial, proximal) to the middle guide wire and parallel to it. A parallel guide can be used. The superior (proximal) guide wire is directed to enter in the superior-anterior part of the femoral head or its superior part. On antero-posterior (AP) view the tip of this guide wire is projected in the superior third part of the femoral head. On lateral view the tip of this guide wire is projected in the anterior third part of the femoral head, but this wire can also be placed more close to the central part of the femoral neck and head, or even in its posterior part, on lateral view.

The guide wire for the inferior (distal) screw is placed in the posterior oblique plane, with an entry point at the median (central or vertical) line of the lateral cortex (supporting point SP2), and 3-7 cm distally (inferiorly, caudally) to the lower border of the greater trochanter or 2-4 cm distally from the middle guide wire, depending on the CCD angle and the femur size. This guide wire is inclined postero-cranially 150-165° (from 140° to 165°) to the diaphyseal axis and directed to the posterior third of the femoral head, so that this guide wire tangentially touches the inferior cortex of the femoral neck on AP view (supporting point SPT) and the posterior cortex of the femoral neck on lateral view (supporting point SP3). On lateral view, this wire enters in the posterior (dorsal) third of the femoral head. On AP view, the tip of this wire is positioned usually between the inferior third part and the superior third part of the femoral head.

Next, drilling along the guide wires and placement of the screws is performed. It is preferable to first place the middle and the superior (proximal) wires and screws, because they are parallel to each-other and are usually perpendicular to the fracture line, however, other sequence of insertion is also applied. The embedding (coupling) of the three screws or some of the screws in a side-plate device or intramedullary nail device is also applicable with the BDSF method and the modified BDSF method.

The specific for the BDSF method and the modified BDSF method are the positions of the screws (implants) and the places of their supporting points described with this method (methods) and its unique biomechanics, and any type of technique or technology can be used to achieve the described positions of the screws (implants), either with or without the use of guide wires, or performing the method(s) either by free placement of the guide wires or screws (implants), (free-hand technique), or by using any type of aiming or targeting devices or instruments or jigs or even by using a computer or robot guidance or control.

The novel aspects in the Modified BDSF method which are different from the initial BDSF method (published in 2011, Filipov) are the following.

1.) With the Modified BDSF method there is defined a new position of the entry point of the inferior guide wire and the inferior screw (1) which new entry point position is defined 'at the median line of the lateral diaphyseal cortex'. This is a very important modification. In the original description in 2011 this entry point was defined 'in the anterior one-third of the surface of the stripped-off diaphysis', whereby in cases with increased femoral neck anteversion (anterior bending of the neck) the screw may fall too posteriorly in the femoral head because in such cases the proper positioning of the screw is prevented by the anterior cortex of the femoral neck. Later, in Filipov 2013, and in Filipov et al. 2017 this entry point was described as 'in the lateral surface of the diaphysis', but not 'at the median line' as described in 2019.

2.) Inclination angle of 120-140° for the middle and superior screws in the Modified BDSF method (compared to 130-140° in the original BDSF method). This is an important modification, because with the old angle of 130-140° in cases with valgus femoral bones the calcar supporting point of the middle screw will be located more lateral and closer to the calcar supporting point of the inferior screw in antero-posterior view. This could lead to physical contact between the screws, resulting in either their malposition in the bone or breakage of the drill bit during drilling. The newly defined inclination angle of 120-140° allows for larger distance between screws and enables for their free passage through the femoral neck.

3.) The sequence of insertion of guide wires in the Modified BDSF method is: first is inserted the middle guide wire; the superior guide wire is inserted second; the distal (inferior) guide wire is inserted last one (in the original BDSF method the sequence is: first the distal (inferior) guide wire is inserted; second—the middle guide wire; last—the superior guide wire). The change of the sequence improves the anatomical orientation of the surgeon and makes the surgery much easier, however, other sequences of insertion are also applicable.

4.) The distance between the middle and superior guide wires (and screws) in the Modified BDSF method is 1.0-3.0 cm (compared to 1.0-2.0 cm in the original BDSF method)

5.) In the Modified BDSF there is described a rule of quarters in that the lateral distance between the shaft of each guide wire and the respective articular surface of the femoral head equator should not be less than one-fifth (⅕) or more than ⅓ of the diameter of the femoral head (not specified in the original BDSF method).

6.) With the Modified BDSF method there is described a Posterior supporting point for the inferior (distal) screw (which is not specified/describer in the original BDSF-method published in 2011). This is a very important modification which substantially improves the fixation strength and resistance to the antero-posterior bending of the femoral neck (when rising from a sitting position or sitting down) which is much powerful than the axial load in errect position (when walking). However the posterior supporting point is described in Filipov 2013 and in Filipov et al., 2017.

Since various modifications can be made in my invention as herein above described, and many apparently widely different embodiments of same made, it is intended that all matter contained in the accompanying specification shall be interpreted as illustrative only and not in a limiting sense.

What is claimed is:

1. A method of fixating a neck fracture of a femur using a modified Biplane Double-Supported Screw Fixation technique (Calcar buttressed screw fixation), said method comprising implanting three fixing screws in positions that, from a lateral view, occupy a neck of said femur in two vertical oblique planes which diverge medially towards a head of said femur at an angle of 15-40° to each-other, and, from among said three fixing screws, implanting an inferior first screw (1) in a posterior one of said oblique planes, with an entry point of said inferior screw at a median line of a lateral diaphyseal cortex of said femur and with an inclination angle of 140-165° to a diaphyseal axis of said femur, and implanting a middle second screw (2) and a superior third screw (3) parallel to one another in an anterior one of said oblique planes, with an inclination angle of 120-140° to the diaphyseal axis of said femur for each of said middle and superior screws, and with a distance of 1.0-3.0 cm between respective screw entry points of said middle and superior screws, wherein placement of the inferior first screw, the middle second screw and the superior third screw comprises use of an inferior guide wire, a middle guide wire and a superior guide wire, respectively, and of said guide wires, the middle guide wire is inserted first, the superior guide wire is inserted second, and the inferior guide wire is inserted last.

2. The method of claim 1 wherein, the inferior first screw (1) and the middle second screw (2) are placed such that each has two supporting points in a distal fracture fragment of said neck fracture, said two supporting points comprising a medial supporting point (SP1) on an inferior cortex of said femoral neck; and a lateral supporting point (SP2) in a lateral cortex of a diaphysis of said femur, at a screw entry hole therein.

3. The method of claim 2 wherein the inferior first screw (1) is also placed so as to also have a third solid supporting point (SP3) on a posterior cortex of the femoral neck, at a spiral anterior curve thereof.

4. The method of claim 2 wherein the inferior first screw (1) and the middle second screw (2) are weight-bearing screws placed such that the medial supporting points (SP1) thereof are located 1-3 cm apart from each-other such that a load borne thereby is distributed over a large area of more than 50% of the inferior cortex of said femoral neck, the medial supporting point (SP1) of the inferior first screw (1) is positioned in a lateral part of the inferior cortex of the femoral neck in proximity to a basicervical line thereof; and the medial supporting point (SP1) of the middle second screw (2) is positioned in a medial part of the inferior neck cortex, in proximity to a midcervical line thereof.

5. The method of claim 1 wherein the middle guide wire and the middle second screw enter the femoral head at an inferior-anterior part thereof; the superior guide wire and the superior third screw enter the femoral head at either a supero-anterior part or superior part thereof; and the inferior first screw enters the femoral head at a posterior third thereof.

6. The method of claim 1 wherein a lateral distance between a shaft of each guide wire and a respective articular surface of an equator of the femoral head is no less than one-fifth and no more than one-third of a diameter of the femoral head.

7. The method of claim 1 wherein during said use of said guide wires, the following steps are performed:
    (A) the middle guide wire is placed in the anterior one of said oblique planes at an angle of 120-140° towards a diaphyseal axis of said femur, and touches on an inferior cortex of said femoral neck, and a tip of the middle guide wire:
  (a) enters the femoral head at an inferior-anterior part thereof;
  (b) from an antero-posterior viewpoint (AP view), projects into an inferior third part of the femoral head; and
  (c) from a lateral viewpoint, projects into an anterior third part of the femoral head;
(B) the superior guide wire is placed in the anterior one of said oblique planes, at a distance of 1.0-3.0 cm superior to the middle guide wire in parallel relation thereto, and enters the femoral head at either a superior part or a superior-anterior part thereof, and a tip of the superior guide wire:
  (d) from said AP view, projects into a superior third part of the femoral head;
  (e) from said lateral viewpoint, occupies a position that:
    (i) projects into an anterior third part of the femoral head;
    (ii) resides generally centrally of the femoral head; or
    (iii) resides in a posterior part of the femoral head;
(C) the inferior guide wire is placed in the posterior one of said oblique planes, with an entry point 2-4 cm inferior from the middle guide wire, at an obtuse angle of 140-165° towards the diaphyseal axis, touches on the inferior cortex of the femoral neck (from said AP view) and touches on the posterior femoral neck cortex (from said lateral viewpoint), and a tip of the inferior guide wire:
  (f) from said lateral viewpoint, enters in a posterior third part of the femoral head; and
  (g) from said AP view, is positioned between the inferior third part and the superior third part of the femoral head; and
(D) after placement of any one or more of the guide wires, in any order, according to any one or more of steps (A) through (C), drilling is performed along said one or more of the guide wires, followed by placement of a respective one or more of the screws.

8. The method of claim 7 wherein the femur is a normal femur, and the middle guide wire is placed at an angle of 130-135° to the diaphyseal axis of said normal femur.

9. The method of claim 7 wherein the femur is a varus femur, and the middle guide wire is placed at an angle of 120-130° to the diaphyseal axis of said varus femur.

10. The method of claim 7 wherein the femur is a valgus femur, and the middle guide wire is placed at an angle of 135-140° to the diaphyseal axis of said valgus femur.

11. The method of claim 7 wherein the inferior guide wire is placed at an angle of 150-165° to the diaphyseal axis of said femur.

12. The method of claim 7 wherein the middle and superior guide wires are placed and drilled along, and the middle second and superior third screws also placed, before placing of the inferior guide wire.

13. The method of claim 7 comprising embedding the three screws in a side-plate device.

14. The method of claim 7 comprising embedding the three screws in an intramedullary nail device.

15. The method of claim 1 wherein the angle at which the two vertical oblique planes diverge medially towards the head of the femur is 20-40°.

* * * * *